US005723686A

United States Patent [19]
Patton et al.

[11] Patent Number: 5,723,686
[45] Date of Patent: Mar. 3, 1998

[54] RECYCLE OF ALCOHOL IN A COMBINED HYDROISOMERIZATION AND ETHERIFICATION PROCESS

[75] Inventors: Gary R. Patton; Robert B. Eldridge, both of Bartlesville, Okla.

[73] Assignee: Phillips Petroleum Company, Bartlesville, Okla.

[21] Appl. No.: 510,988

[22] Filed: Aug. 3, 1995

[51] Int. Cl.$^6$ ..................... C07C 41/42
[52] U.S. Cl. ..................... 568/697
[58] Field of Search ..................... 568/697

[56] References Cited

U.S. PATENT DOCUMENTS

| | | | |
|---|---|---|---|
| 3,135,807 | 6/1964 | Grasselli et al. | 260/614 |
| 3,846,088 | 11/1974 | Brown et al. | 44/56 |
| 3,979,461 | 9/1976 | Ancillotti et al. | 260/614 |
| 4,071,567 | 1/1978 | Ancillotti et al. | 260/614 |
| 4,490,563 | 12/1984 | Van Pool et al. | 568/697 |
| 5,237,115 | 8/1993 | Makovec et al. | 585/314 |
| 5,329,051 | 7/1994 | Eason et al. | 568/699 |

FOREIGN PATENT DOCUMENTS 0 605 822 A1  7/1994  European Pat. Off. .

*Primary Examiner*—Gary Geist
*Assistant Examiner*—S. Padmanabhan
*Attorney, Agent, or Firm*—Ryan N. Cross

[57] ABSTRACT

A combination process wherein a hydroisomerization system provides a hydrocarbon feed for an etherification system wherein unreacted alcohol is separated from the etherification effluent and passed to the fractionation column used in the hydroisomerization system so that water entrained in the unreacted alcohol can be separated from said alcohol within said fractionation column.

8 Claims, 1 Drawing Sheet

RECYCLE OF ALCOHOL IN A COMBINED HYDROISOMERIZATION AND ETHERIFICATION PROCESS

This invention relates to the recycle of unreacted alcohols in etherification processes. In one aspect it relates to a method of recovering unreacted alcohols from the etherification effluent of a combined hydroisomerization and etherification process and to subsequent recycling of the unreacted alcohols for further use in the combined process.

BACKGROUND OF THE INVENTION

It is known that tertiary-alkyl ethers, which are high octane blending components for motor fuels, can be prepared by reacting a primary alcohol with an olefin having a double bond on the tertiary carbon atom. For example, methanol reacts with isobutylene or isoamylene to form respective methyl tertiary-butyl ether (MTBE) and tertiary-amyl methyl ether (TAME). Similar reactions are known which produce ethyl tertiary-butyl ether (ETBE) and tertiary-amyl ethyl ether (TAEE). Reference is had to U.S. Pat. Nos. 4,071,567; 3,979,461; 3,135,807; 3,846,088; among many others.

These ether reactions are so selective for tertiary olefins that they constitute a valid process for the removal of tertiary olefinic streams where they are encountered together with linear olefins. When producing such ethers, however, it is desirable to remove the unreacted alcohol from the ether in the reaction effluent and recycle it to the ether reactor.

Typically, in the case of etherification processes using ethanol, the alcohol is separated from the etherification reaction effluent by water extraction. The resulting water/alcohol mixture is sent to a fractionator to recover alcohol for recycle to the ether reactor and water for use in the extraction step. The recovered alcohol, however, will still contain some water after the fractionation. Typically, the recovered alcohol will contain up to about 5% water for etherification processes producing ETBE and TAEE. The etherification reaction kinetics are such that even a small water content can result in a significant loss of conversion for the catalyst. For example, ETBE reaction kinetics are such that water content in the feed in the range of 1,000 to 2,000 parts per million will result in a loss up to about 3% conversion across the catalyst.

Even if water extraction is not utilized, the ether reaction may be accompanied by several unwanted by-product reactions, some of which produce water. Therefore, it is still necessary to strip the water from the alcohol prior to recycle of the alcohol to the etherification reactor.

Prior etherification processes have required extractive distillation or absorption of the alcohol after it has undergone the fractionation in order to remove the remaining water. However, such an extractive distillation or absorption step significantly increases the cost of the etherification unit.

Accordingly, it is an object of this invention to provide a process which will recover alcohol from an etherification reactor effluent at a reduced cost compared to prior recovery systems.

Another object is to provide a process for the recovery and recycling of alcohol in a combined hydroisomerization and etherification system wherein the recycled alcohol is substantially free of water when it is introduced into the etherification unit.

BRIEF SUMMARY OF THE INVENTION

In accordance with this invention there is provided a method of processing hydrocarbon feed containing olefin compounds and diolefin compounds in a combined hydroisomerization and etherification system wherein unreacted alcohol is separated from the etherification effluent and passed to a fractionator which separates the hydroisomerization effluent stream subsequent to the hydroisomerization. The method comprises the steps of hydroisomerizing the hydrocarbon feed in a first hydroisomerizing zone so as to hydrogenate diolefin compounds to olefin compounds and to produce a reaction effluent comprising the olefin compounds, unreacted hydrocarbons and light compounds; separating a hydroisomerate stream comprising the olefin compounds from the reaction effluent in a first separation zone; combining the hydroisomerate stream with an alcohol feed to produce a combined stream; etherifiying said combined stream in an etherification zone to produce an oxygenate stream comprising oxygenated compounds, unreacted alcohol and unreacted hydrocarbons; separating the oxygenated stream into at least three streams in a second separation zone under conditions which provide a first stream comprising a product stream of said oxygenated compounds, a second stream which comprises said unreacted hydrocarbons and a third stream which comprises water and unreacted alcohol; and passing the third stream to the first separation zone.

Other objects, aspects, and features of the present invention will be evident from the following detailed description of the invention, the claims and the drawing in which:

DETAILED DESCRIPTION OF THE INVENTION

Figure 1:
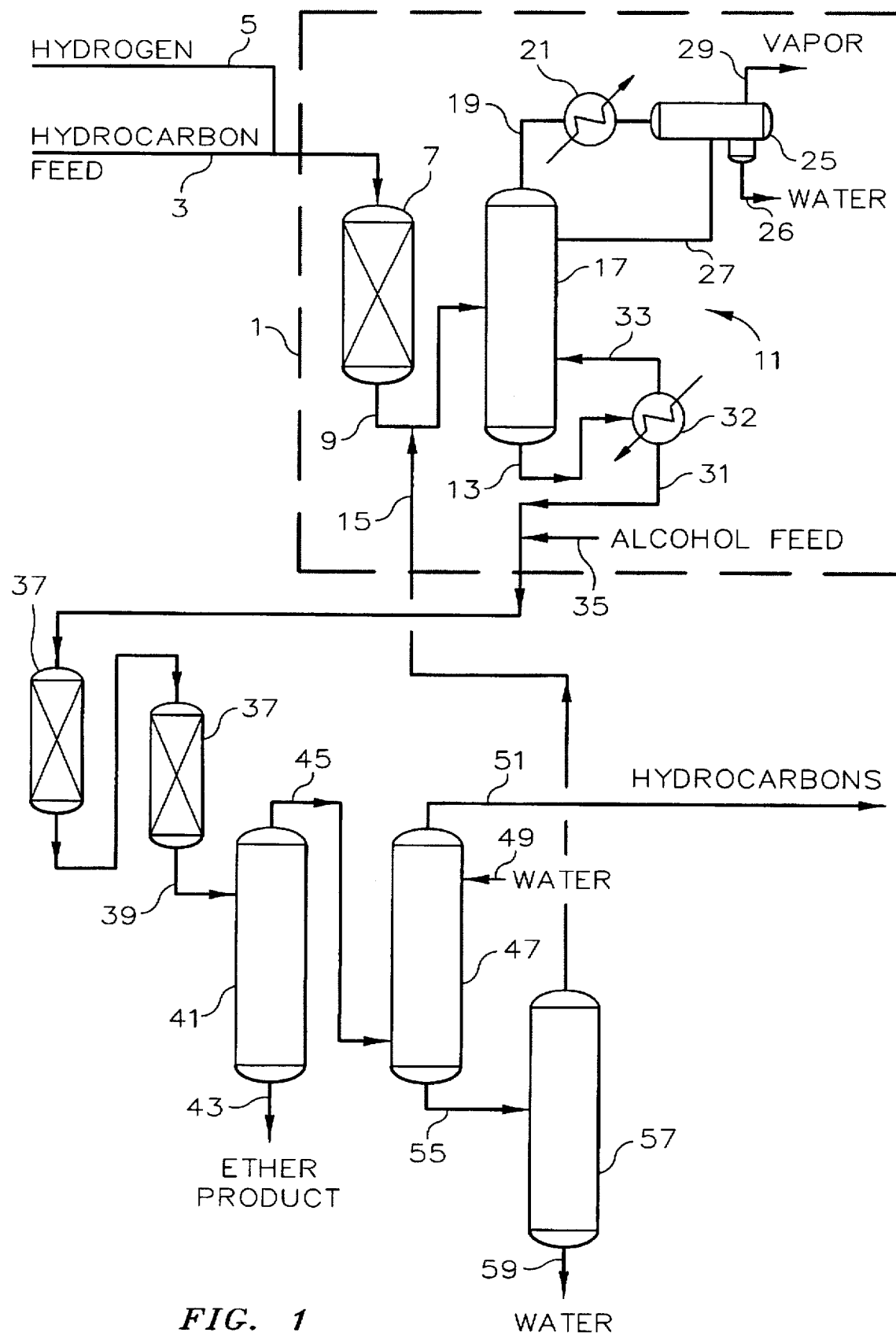
FIG. 1 is a simplified schematic illustration showing a process flow and arrangement of an apparatus according to a preferred embodiment of this invention.

It will be appreciated by those skilled in the art that FIG. 1 is schematic only and many items of equipment which would be needed in a commercial plant for successful operation have been omitted for the sake of clarity. Such items of equipment would include, for example, flow, pressure, and temperature measuring instruments with corresponding process controllers; pumps, heat exchangers, valves, etc. All these items would be provided in accordance with standard chemical engineering practice; however, they play no part in the explanation of the present invention.

The present invention is applicable to integrated olefin processing schemes wherein olefins are processed to produce high octane gasoline blending components. Applicable processing schemes should utilize a hydroisomerization component and an etherification component. The hydroisomerization component should comprise a hydroisomerization zone and a hydroisomerization separation zone. The etherification components should comprise an etherification zone and a etherification separation zone, preferably utilizing water extraction to remove unreacted alcohol from other components of the etherification zone effluent such as unreacted hydrocarbons. A suitable integrated process is disclosed in U.S. Pat. No. 5,237,115 the disclosure of which is incorporated herein by reference.

Although the present invention is applicable to most such integrated olefin processing schemes, it is particularly applicable to ones which utilize ethanol in the etherification component to produce ETBE or TAEE. This is because in the case of ETBE and TAEE production, the azeotropes that form between ethanol and hydrocarbons make the substantial recovery of ethanol, along with the ETBE or TAEE bottoms product from the etherification reaction product fractionator, difficult. Specifically, the presence of ethanol in an etherification reaction zone product stream often causes difficulty in separation of the ether product due to the azeotropic compositions formed with the hydrocarbons and ethers of the etherification reaction zone product stream.

The amount of alcohol contained in the etherification reaction zone product stream is generally set by the concentration of isobutylene contained in the etherification reaction zone feed. As the concentration of isobutylene increases, the stoichiometric requirement of alcohol reactant correspondingly increases. Therefore, as the alcohol concentration in the etherification reaction zone feed increases, there is also a corresponding increase in the amount of alcohol contained in the etherification reaction zone product stream.

The etherification reaction zone product stream is charged or fed to a fractionation column which defines a separation zone and provides for the separation of such etherification reaction zone product stream, or reaction product, into an overhead product containing a non-reactive and/or unreacted hydrocarbons and a bottoms product containing the ether product.

In a typical etherification process operation, it is more desirable to produce a fractionator bottoms product comprising ether that is substantially free of alcohol. Thus, in conventional ether processes, the fractionator overhead product preferably contains most of the alcohol contained in the etherification reaction zone product stream. The presence of ethanol in the fractionator overhead product has two disadvantages. One disadvantage is associated with the difficulty in effectively removing ethanol from the fractionator overhead product prior to passing the resultant ethanol-free hydrocarbons to downstream processing units such as HF alkylation. A small amount of ethanol in the feed of some of the downstream processing units can have an enormous detrimental impact on such units. A key problem with performing a fractional separation between the non-reactive hydrocarbons and ethanol of the etherification reaction zone product stream is the formation of azeotropes, also known as constant boiling mixtures, which prevent a satisfactory separation of the two components. Another disadvantage to the presence of large quantities of ethanol in the fractionator overhead product is simply the undesirable lack of recovery of ethanol as a fractionator bottoms product.

In order to overcome these problems, the overhead product can be treated by a water extraction, or water wash, process, wherein water, acting as a solvent, and the overhead product are introduced into an extractor in order to separate the ethanol from the hydrocarbons. However, before the ethanol can be recycled, the water must be removed in order to prevent degradation of the etherification catalyst. Fractionation of the water/ethanol mixture leaves a minor but significant amount of water with the ethanol. This minor amount of water can be removed by adsorption or extractive distillation. However, in the instant invention, as further described below, a more cost efficient system is utilized wherein the hydroisomerization fractionator is used to separate the water from the ethanol prior to recycle.

While the invention, as described below, is especially applicable to etherification systems utilizing ethanol as the alcohol, it can also be used successfully with other alcohols such as methanol.

Referring now to FIG. 1, a combination hydroisomerization and etherification system utilizing the present invention is illustrated. A hydrocarbon stream is conveyed to the hydroisomerization system 1 through line 3. The hydrocarbon feed comprises olefin compounds and diolefin compounds, preferably $C_4$ and/or $C_5$ olefin compounds depending on the type of tertiary-alkyl ethers that it is desired to produce. Hydrogen is conveyed by way of conduit 5 and mixed with the hydrocarbon feed stream that is passing through conduit 3 prior to the resultant mixture entering hydroisomerization reactor 7, which defines a hydroisomerization zone. Within the hydroisomerization reactor 7, hydrocarbons undergo hydroisomerization. The term "hydroisomerization" as used herein, refers to the conversion of a hydrocarbon feed stream in the presence of hydrogen wherein diolefins are selectively hydrogenated to olefins and hydrocarbons, containing at least one acyclic terminal monoolefin having from 4 to about 7 carbon atoms per molecule, are isomerized to hydrocarbons which contain at least one acyclic internal monoolefin having the same number of carbon atoms. Preferred feed streams include those comprising mixtures of isobutene and butene-1, isopentene and pentene-1, and the like.

The reactor effluent from hydroisomerization reactor 7 passes by way of conduit 9 to a separation system 11 wherein a hydroisomerate stream is separated from the reactor effluent and passes from hydroisomerization system 1 via conduit 31. Additionally, recycle alcohol, containing a minor portion of water, is introduced into hydroisomerization system 1 via conduit 15 and mixed with the reactor effluent from hydroisomerization reactor 7 that is passing through conduit 9 prior to the resulting mixture entering separation system 11. Optionally, the alcohol and water stream can be introduced directly into separation system 11.

Within separation system 11 the hydroisomerization reaction effluent and the recycle alcohol and water are introduced into a separation vessel 17, defining a first separation zone, wherein the light hydrocarbons and water contained in the mixture introduced into vessel 17 are separated from the alcohol and olefins. The term light hydrocarbons, as used herein, generally refers to hydrocarbons having boiling points lower than the alcohol and olefins that are desired to be reacted in the etherification reactor and includes hydrogen, methane, ethane, propylene, propane and the like. The light hydrocarbons and water are removed from the top of separation vessel 17 through conduit 19 as an overhead vapor stream. The vapor stream is indirectly cooled and hydrocarbons other than lights are substantially all condensed in condenser 21. The vapor stream along with the condensed hydrocarbons are passed via conduit 23 to accumulator 25. A reflux stream is withdrawn from accumulator 25 via conduit 27 and returned to separation vessel 17. Additionally, an off-take stream removes light hydrocarbons via conduit 29 and water is removed via conduit 26.

Within separation vessel 17, the water is stripped from the alcohol so that substantially all the water is separated from the alcohol. Thus, the stream removed off the bottom of separation vessel 17 contains at most only trace amounts of water.

The hydroisomerate stream is removed off the bottom separation vessel 17 via conduit 13. The hydroisomerate stream comprises olefins and alcohol. More specifically the hydroisomerate stream will generally comprise propylene, isobutylene, butylenes, amylenes, ethanol and/or methanol. The hydroisomerate stream is introduced into reboiler 32 via conduit 13 and heated in reboiler 32 with a vapor portion being returned to separation vessel 17 via conduit 33 and a liquid portion passing from hydroisomerate system 1 via conduit 31.

The hydroisomerate stream, which passes from hydroisomerization system 1 via line 31 is mixed with additional alcohol, typically methanol and/or ethanol, that is introduced via conduit 35 to form a combine stream. The resultant combine stream is charged to at least one etherification reactor 37 which defines at least one etherification zone. Within the etherification zone, the components of the combine stream are etherified. Generally, this involves the conversion of iso-olefins having tertiary carbon atoms to ethers by reaction with primary or secondary alcohols in the presence of an acid ion exchange resin catalyst. The etherification reactor effluent passes by way of conduit 39 to a second separation zone, generally comprising at least an ether fractionator and an extraction column. The effluent first enters ether fractionator 41 wherein an oxygenated stream is separated from unreacted compounds. The oxygenated stream, or product stream, may comprise MTBE, TAME, ETBE, and/or TAEE depending on the olefins and alcohol chosen for charge to reactor 37. The oxygenated stream is conveyed from etherification fractionator 41 via conduit 43. The unreacted compounds pass by way of conduit 45 to extraction column 47. The extraction column or so called water washing operation, involves countercurrently contacting the unreacted compounds with water supplied via conduit 49 at a temperature typically about 40° C. and a gauge pressure, e.g., 1,000 to 1,200 kPa, which is sufficient to keep the hydrocarbon contained in the unreacted components in a liquid phase. Within the extraction column 49 unreacted alcohol and unreacted hydrocarbon compounds are separated. The unreacted hydrocarbon compounds pass from extraction column 47 via conduit 51 and can be further processed, such as in an HF alkylation unit, if desired.

Alcohol and water are removed from extraction column 47 via conduit 55 and introduced to separation vessel 57 wherein a major portion of the water is separated from the alcohol. Water is remove from separation vessel 57 via conduit 59 and alcohol and a minor portion of water are removed from the tops of separation vessel 57 via conduit 15. The alcohol removed via conduit 15 will generally contain less than 10% by volume water based on the volume of the stream removed via conduit 15. Typically, the alcohol will contain up to about 5% by volume water. The alcohol stream removed via conduit 15 is introduced to separation vessel 17 wherein the water is stripped from the alcohol as previously described.

The inventive process above is most beneficial in etherification processes using an alcohol which form azeotropes, as described above, and which has a high affinity for water. Thus, it is more useful in etherification processes utilizing ethanol than in those utilizing methanol.

The following example is a calculated example using ethanol as the alcohol and ethyl t-butyl ether (ETBE) as the etherification product.

| CALCULATED EXAMPLE | |
|---|---|
| Calculated Operating Conditions: | |
| (17) Separation System | |
| Temperature at inlet, °F., | 150 |
| Temperature at outlet (13), °F., | 244 |
| Temperature at off-take conduit (29), °F., | 167 |
| Temperature at off-take conduit (26), °F., | 168 |
| Pressure at inlet, psia, | 350 |
| Pressure at outlet (13), psia, | 345 |
| Pressure at off-take (29), psia, | 330 |
| Pressure at off-take (26), psia, | 330 |

| CALCULATED EXAMPLE -continued | | |
|---|---|---|
| (35) Alcohol Feed Stream | | |
| Temperature, °F., | | 100 |
| Pressure, psia, | | 150 |
| (43) Ether Product Stream | | |
| Temperature, °F., | | 270 |
| Pressure, psia, | | 150 |
| (15) Alcohol Recycle Stream | | |
| Temperature, °F., | | 183 |
| Pressure, psia, | | 350 |
| (51) Unreacted Hydrocarbon Stream | | |
| Temperature, °F., | | 101 |
| Pressure, psia, | | 150 |
| Calculated Flow Rates: | Constituent (lb mol/hr) | Total (lb mol/hr) |
| Into Separation Vessel (17) | | 2331.2 |
| Butanes (I-Butane and N-Butane) | 776.1 | |
| Butenes | 1328.3 | |
| (1-Butene, Cis-2 Butene, Trans-2-Butene, and 7-Butene) | | |
| Pentanes | 73.1 | |
| (I-Pentane and N-Pentane) | | |
| Ethanol | 36.4 | |
| Water | 39.6 | |
| ETBE | 0.0 | |
| Other | 77.7 | |
| At off-take (29) | | 49.4 |
| Butanes | 6.4 | |
| Butenes | 6.6 | |
| Pentanes | 0.0 | |
| Ethanol | 0.8 | |
| Water | 0.6 | |
| ETBE | 0.0 | |
| Other | 35.0 | |
| At off-take (26) | | 39.0 |
| Water | 39.0 | |
| At outlet (13) | | 2242.8 |
| Butanes | 769.7 | |
| Butenes | 1321.7 | |
| Pentanes | 73.1 | |
| Ethanol | 35.6 | |
| Water | 0.0 | |
| ETBE | 0.0 | |
| Other | 42.7 | |
| Alcohol Feed (35) | | 344.0 |
| Ethanol | 344.0 | |
| Ether Product (43) | | 304.3 |
| ETBE | 304.0 | |
| Other | .3 | |
| Alcohol Recycle Stream (15) | | 72.8 |
| ETBE | 36.4 | |
| Water | 36.1 | |
| Other | .3 | |
| Unreacted Hydrocarbon Stream (51) | | 1905.5 |
| Butanes | 769.7 | |
| Butenes | 1013.7 | |
| Pentanes | 73.1 | |
| Ethanol | 0.1 | |
| Water | 2.9 | |
| ETBE | 3.1 | |
| Other | 42.9 | |

Reasonable variations and modifications which will become apparent to those skilled in the art, can be made in That which is claimed:

1. A method of processing a hydrocarbon feed containing olefin compounds and diolefin compounds comprising:

(a) hydroisomerizing said hydrocarbon feed in a first hydroisomerization zone so as to hydrogenate diolefin compounds to olefin compounds and to produce a reaction effluent comprising said olefin compounds, unreacted hydrocarbons and light hydrocarbons;

(b) separating a hydroisomerate stream comprising said olefin compounds from said reaction effluent in a first separation zone;

(c) combining said hydroisomerate stream with an alcohol feed to produce a combine stream;

(d) etherifying said combine stream in an etherification zone to produce an oxygenate stream comprising oxygenated compounds, unreacted alcohol and unreacted hydrocarbons;

(e) separating said oxygenated stream into at least three streams in a second separation zone under conditions which provide a first stream comprising a product stream of said oxgenated compounds, a second stream which comprises said unreacted hydrocarbons and a third stream which comprises unreacted alcohol and water; and (f) passing said third stream to said first separation zone.

2. A method according to claim 1 wherein within said first separation zone water is stripped from said alcohol such that said hydroisomerate stream comprises said olefin compounds and said alcohol and is substantially free of water.

3. A method according to claim 1 wherein said third stream is formed by counter currently contacting said alcohol and said unreacted hydrocarbons contained in said oxygenated stream with water in an extraction column so that said alcohol is separated from said unreacted reacted hydrocarbons.

4. A method according to claim 1 wherein said alcohol is ethanol.

5. A method according to claim 4 wherein said hydrocarbon feed comprises unsaturated hydrocarbons having from 3 to 6 carbon atoms per molecule, propylene, isobutylene, butadiene, butylenes and amylenes.

6. A method according to claim 1 wherein said etherifying in step (d) utilizes said ethanol as a reactant to react with isobutylene and/or amylene contained in said hydroisomerate stream to produce said oxygenate stream comprising ethyl tertiary butyl ether (ETBE) and/or tertiary amyl ethyl ether (TAEE), respectively.

7. A method according to claim 1 wherein said oxygenated stream is separated into at least four streams in step (e) under conditions which provide a fourth stream which comprises substantially water.

8. A method according to claim 7 wherein said third stream comprises alcohol and up to about five volume percent water based on the total volume of said third stream.

* * * * *